United States Patent
Schatz et al.

(10) Patent No.: US 8,038,439 B2
(45) Date of Patent: Oct. 18, 2011

(54) MEDICAL HANDPIECE WITH A LIGHTING DEVICE

(75) Inventors: Norbert Schatz, Burmoos (AT); Karl Schmiedlechner, Ostermiething (AT)

(73) Assignee: W&H Dentalwerk Burmoos GmbH (AT)

(*) Notice: Subject to any disclaimer, the term of this patent is extended or adjusted under 35 U.S.C. 154(b) by 399 days.

(21) Appl. No.: 11/998,134

(22) Filed: Nov. 27, 2007

(65) Prior Publication Data

US 2008/0131835 A1 Jun. 5, 2008

(30) Foreign Application Priority Data

Nov. 30, 2006 (EP) .................................... 06024780

(51) Int. Cl.
*A61C 1/00* (2006.01)
(52) U.S. Cl. .......................................................... 433/29
(58) Field of Classification Search ............... 433/29, 433/114, 126
See application file for complete search history.

(56) References Cited

U.S. PATENT DOCUMENTS

| | | | | |
|---|---|---|---|---|
| 4,680,011 A | * | 7/1987 | Boinot | 433/29 |
| 5,908,295 A | * | 6/1999 | Kawata | 433/29 |
| 6,161,937 A | * | 12/2000 | Rosenstatter | 362/109 |
| 6,561,972 B2 | * | 5/2003 | Ooshima et al. | 600/173 |
| 2008/0108010 A1 | * | 5/2008 | Wang | 433/29 |

FOREIGN PATENT DOCUMENTS

| | | |
|---|---|---|
| EP | 0 199 390 | 10/1986 |
| EP | 0 884 025 | 12/1998 |
| EP | 1 693 021 | 8/2006 |
| JP | 10-165419 | 6/1998 |

OTHER PUBLICATIONS

European Search Report for EP 06 02 4780.

* cited by examiner

*Primary Examiner* — Cris L Rodriguez
*Assistant Examiner* — Eric Rosen
(74) *Attorney, Agent, or Firm* — Klarquist Sparkman, LLP

(57) ABSTRACT

There is disclosed a medical handpiece, in particular a dental handpiece, having a lighting device which includes at least one optical semiconductor element, whereby the at least one optical semiconductor element is arranged at least partially in the interior of the handpiece and is detachably connected to the handpiece. On account of this design, it is possible for the user to easily connect the handpiece to an optical semiconductor element that is needed for a certain treatment and has, for example, a certain desired power level and/or emits a desired wavelength. The handpiece may thus be used for different applications without requiring any additional components such as switches, etc., that take up space. The outside dimensions of the handpiece remain substantially unchanged in comparison with known handpieces.

36 Claims, 2 Drawing Sheets

MEDICAL HANDPIECE WITH A LIGHTING DEVICE

CROSS REFERENCE TO RELATED APPLICATION

The present application claims priority from pending European Patent Application No. 06024780.6, filed Nov. 30, 2006, which is incorporated herein by reference.

BACKGROUND

1. Field

The present application relates to a medical handpiece, in particular a dental handpiece, having a lighting device comprising at least one optical semiconductor element.

2. Description of Prior Art

Japanese Patent Application JP 10165419 A describes a dental handpiece having a lighting device capable of emitting radiation of different wavelengths to thereby be able to perform different treatments. The handpiece therefore comprises multiple light sources in the form of LEDs and a switch by means of which optionally one or more LEDs can be operated so that green or blue light, for example, is emitted for treatments or white light is emitted for illuminating the treatment site.

One disadvantage is that the design of this handpiece is complicated and requires a great deal of space because multiple LEDs, a switch and electronic or mechanical switch elements have to be accommodated in the handpiece. Because of a wide variety of components contained in the handpieces with a connection for tools that can be set in motion, e.g., drive elements, tool receptacles, media lines, etc., integration of additional elements is not possible to an unlimited extent or would be possible only if the outside dimensions of the handpiece could be enlarged. However, the space available in the oral cavity is very limited, especially for dental applications, and the user's vision is often limited to the preparation site, so larger outside dimensions are not desirable.

One object is thus to create a medical handpiece, in particular a dental handpiece, having a receptacle for tools that can be set in motion and having a lighting device with which treatments can be performed under different operating parameters, e.g., different wavelengths, whereby the handpiece should have the simplest possible design and there should not be any increase in the outside dimensions of the handpiece.

SUMMARY

According to one embodiment, the medical handpiece, in particular dental handpiece, has a lighting device with at least one optical semiconductor element, whereby the at least one optical semiconductor element is arranged at least partially in the interior of the handpiece and whereby it is detachably connected to the handpiece. Due to this design, it is possible for the user to easily connect the handpiece to the optical semiconductor element, which is needed for the respective treatment and has, for example, a certain desired power level and/or emits a desired wavelength. The handpiece may thus be used for different applications without requiring additional components that take up space, such as switches, etc. The outside dimensions of the handpiece thus remain unchanged in comparison with known handpieces.

Due to the arrangement of the at least one optical semiconductor element at least partially in the interior of the handpiece, this also ensures that the optical semiconductor element does not hinder or impair the handling of the handpiece. In a preferred embodiment, the electric components which supply electricity to the optical semiconductor element, in particular cables and contacts, are accommodated in the handle, thereby further improving the handling of the handpiece.

Another advantage of the inventive handpiece is that the at least one optical semiconductor element can easily be replaced if it is damaged and no longer functional. This may occur in particular due to the penetration of particles, liquids or gases, e.g., liquid or gaseous cleaning media through the lighting device to the optical semiconductor element. In replacement, thus only the optical semiconductor element that is no longer functional is replaced, whereas the functional handpiece may remain in use.

In addition, the inventive handpiece may be used for various treatments for which users have previously required multiple handpieces. Thus the cost of acquisition as well as the cleaning and maintenance cost for the user are reduced.

The detachable connection of the at least one optical semiconductor element to the handpiece can be established by all known detachable connecting means, e.g., by a form-fitting or frictionally locking connection, or by clamped, screw or plug connections.

To be able to detach the at least one optical semiconductor element from the handpiece and remove it, the handpiece may be designed in two pieces, with the separation point between the two handpiece parts preferably being provided approximately at the location where the semiconductor element is arranged, so that it is readily accessible. The head and handle part of the handpiece in particular may be detachable from one another and the at least one optical semiconductor element may be arranged in the area of the separation point.

In a preferred embodiment, an opening which is provided in the outer sleeve of the handpiece is designed so the at least one optical semiconductor element can be passed through this opening. This eliminates the need for a two-piece design of the handpiece with an additional separation point and with corresponding connecting means and sealing means. The opening in particular must be large enough so that the at least one optical semiconductor element can be passed through it, and it must be arranged at a location on the outer sleeve to which the optical semiconductor element has access in particular from the interior of the handpiece or toward which it moves, e.g., toward which it can be pushed, and it should also be provided at a location on the handpiece that is readily accessible from the outside, so that the optical semiconductor element can be passed through the opening in a manner that is easy for the user.

An opening which also fulfills another function is especially preferably used as the opening for passing the optical semiconductor element through, so that no additional opening for passing an optical semiconductor element through need be provided in the outer sleeve of the handpiece. Such an opening may be, for example, the light-emitting opening or the coupling opening. If the handpiece includes an accommodation for a battery with an opening through which a battery can be inserted, then the optical semiconductor element may also be inserted into the handpiece or removed from it through this opening.

In another embodiment, the handpiece is designed so that the at least one optical semiconductor element can be moved through an interior space of the handpiece, in particular to an opening provided in the outer sleeve of the handpiece through which the optical semiconductor element can be passed, i.e., can be removed from and inserted into the handpiece. To this end, either corresponding passages, openings or clearances may be provided in the interior of the handpiece and between components arranged therein and/or one or more components arranged in the handpiece may be removed from the handpiece or may be movably arranged therein, so that the optical semiconductor element can be moved through the interior of the handpiece after removing these components.

In particular, it is possible to provide for the head part of the handpiece to be arranged movably, e.g., displaceably in relation to the handle part so that the optical semiconductor element which is clamped in place in the handpiece by the head part is movable in the handpiece. In addition, one or more components, e.g., coupling elements for connection of the handpiece to a power supply or drive unit or media lines, may be arranged on the handpiece or in the interior of the handpiece, so that they are displaceable or can be removed from the handpiece, thereby permitting or facilitating access to the optical semiconductor element to be replaced or its removal from the handpiece.

In a preferred embodiment, the at least one optical semiconductor element is designed as part of a lighting module, in particular a lighting module that is hermetically sealed from the outside, whereby the at least one optical semiconductor element is releasable from the handpiece jointly with the lighting module. Integration of the at least one optical semiconductor element into a lighting module has several advantages. For example, the lighting module may be provided with additional function elements, e.g., one or more fastening means for detachable connection of the lighting module to the handpiece. In addition, a rotational lock or form-fitting elements may also be provided to prevent twisting of the lighting module and/or facilitate the insertion and/or attachment of the lighting module and the optical semiconductor element in only one selected position. This is important in particular for a correct connection of the optical semiconductor element to the power source. Sealing elements or means, e.g., for sealing the interior space of the handpiece from the environment, waveguides, light-emitting windows, protective glasses or a casting material that encases, connects and seals the electric contacts of the at least one optical semiconductor element and the electric lines or contacts connected to them may also be provided on the lighting module.

The lighting module is preferably hermetically sealed from the outside and/or comprises a hermetically sealed interior space in which the at least one optical semiconductor element is accommodated. Therefore, the optical semiconductor element is protected from damage, penetration of substances, etc. The hermetic seal is especially preferably designed so that the optical semiconductor element is sterilizable, i.e., can withstand repeated introduction into an environment at temperatures of at least 120° C., preferably 130° C., especially preferably 134° C. and/or with steam or chemicals or gases, in particular disinfectants, and/or pressure fluctuations of approximately 1 bar without being damaged. The hermetic seal may be provided by encapsulation of the at least one optical semiconductor element with metallic and/or plastic elements. It may also be achieved by covering the at least one optical semiconductor element with curable plastics or resins, e.g., epoxy resins.

In addition, multiple optical semiconductor elements may also be present in the lighting module, so that a higher light output is achievable. At the same time, the use of the optical semiconductor elements is facilitated because most of the optical semiconductor elements can be handled jointly, e.g., are replaceable.

In a preferred embodiment, the lighting device of the handpiece is connected to other components, e.g., to a waveguide and/or to an optical element, e.g., a lens, and in particular to electric or electronic components such as an electric line and/or electric contacts and/or a carrier device, preferably a circuit board, and/or electric coupling elements and/or electric or electronic components such as rectifiers, resistors, transformers, etc., at least one of these components can be released from the handpiece together with the at least one optical semiconductor element or the lighting module.

The component that is replaceable and jointly attachable together with the optical semiconductor element or the lighting module is especially preferably the electric lines or contacts that are used for connecting the optical semiconductor element or the lighting module to an electric power source. If the optical semiconductor element or the lighting module can be released from the handpiece together with the electric lines or contacts, then the optical semiconductor element or the lighting module and the electric lines or contacts are joined together fixedly, i.e., undetachably, e.g., by soldering, welding and/or by an encasing material, e.g., a casting material, in particular being inseparably encased by a synthetic resin such as epoxy resin or silicone resin.

This nonreleasable connection has the advantage that the optical semiconductor element or the lighting module can be introduced into the handpiece only in a certain position, namely in such a way that a connection to the power supply or electric current source can be established via the lines or contacts, in particular so that the lines or contacts are facing the current source. This creates a possibility for inserting the optical semiconductor element into the handpiece in such a way that it is correctly connected to the power supply, i.e., the positive and negative poles of the optical semiconductor element are each connected to the positive and negative poles, respectively, of the d.c. current source, so that the connection to the current source is established according to the direction of current flow of the optical semiconductor element. This advantageously makes it possible to prevent the user of the optical semiconductor element or the lighting module from inserting the optical semiconductor element or the lighting module into the handpiece in a random position and then having to check on whether the optical semiconductor element or the lighting module has been attached correctly, i.e., in the correct direction of current flow in the handpiece, and if this is not the case, the optical semiconductor element or the lighting module having to be removed from the handpiece again and reinserted in another position.

The introduction of the lighting module in a predetermined position into the handpiece has other advantages, e.g., if the lighting module comprises an optical element, preferably a lens that focuses the radiation generated by the optical semiconductor element at a specific point, in particular the point of the tool chucked in the handpiece. If the lighting module can be inserted into the handpiece in only one position, this also reliably ensures that the lens is arranged in the handpiece in such a way that it deflects the radiation in the desired direction and onto the desired point.

In another embodiment, a circuit, in particular an electronic circuit, may additionally be provided in the handpiece, so that the electronic circuit receives the energy supplied by the current source and adapts it to the requirements of the at least one optical semiconductor element. In particular it receives the current of the current source regardless of its polarity and delivers it with a defined polarity, which is suitable for the optical semiconductor element connected to the circuit. To do so, a polarization protection circuit, for example, consisting of a plurality of diodes and optionally additional elements, in particular a so-called bridge circuit or a bridge rectifier circuit may be provided. The circuit may also contain other elements such as rectifiers, transformers, converters, resistors, etc., to process the amperage or voltage in particular in such a way that it is suitable for the connected semiconductor element. Such an optical semiconductor element, e.g., an LED is usually operated with a d.c. current of approximately 2-3 V and at least 20 mA, preferably more than 50 mA.

However, the circuit need not necessarily be provided in the handpiece but instead may also be contained in other instruments or devices that are or can be connected to the handpiece so that the electric current reaching the handpiece already has a defined polarity and suitable current parameters, respectively.

The above embodiments and others are explained in greater detail below and with reference to the accompanying drawings, in which:

DETAILED DESCRIPTION

Figure 1:
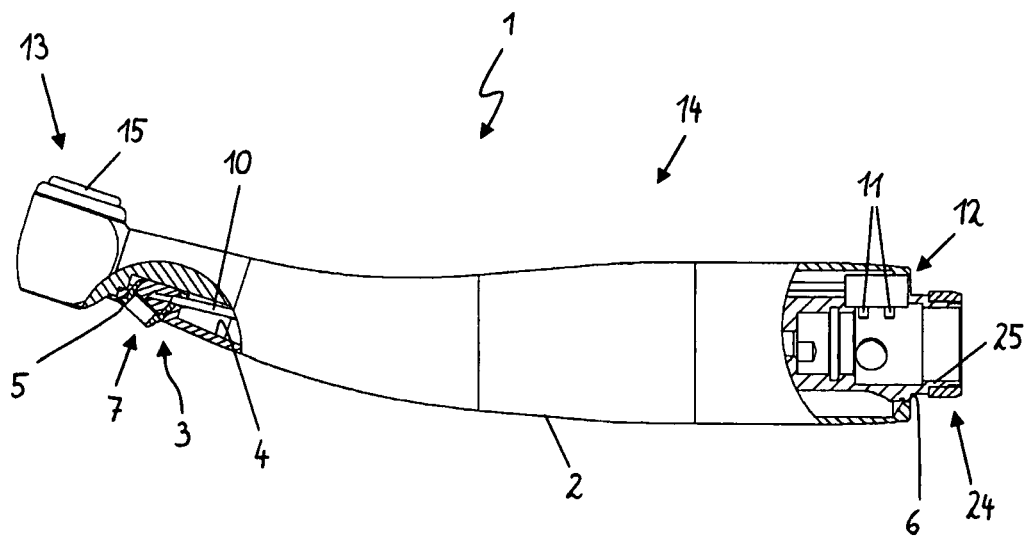
FIG. 1 shows a first preferred embodiment of a medical handpiece, in particular a dental handpiece, partially in section, with a lighting device comprising at least one optical semiconductor element that can be detached from the handpiece.
Figure 2:
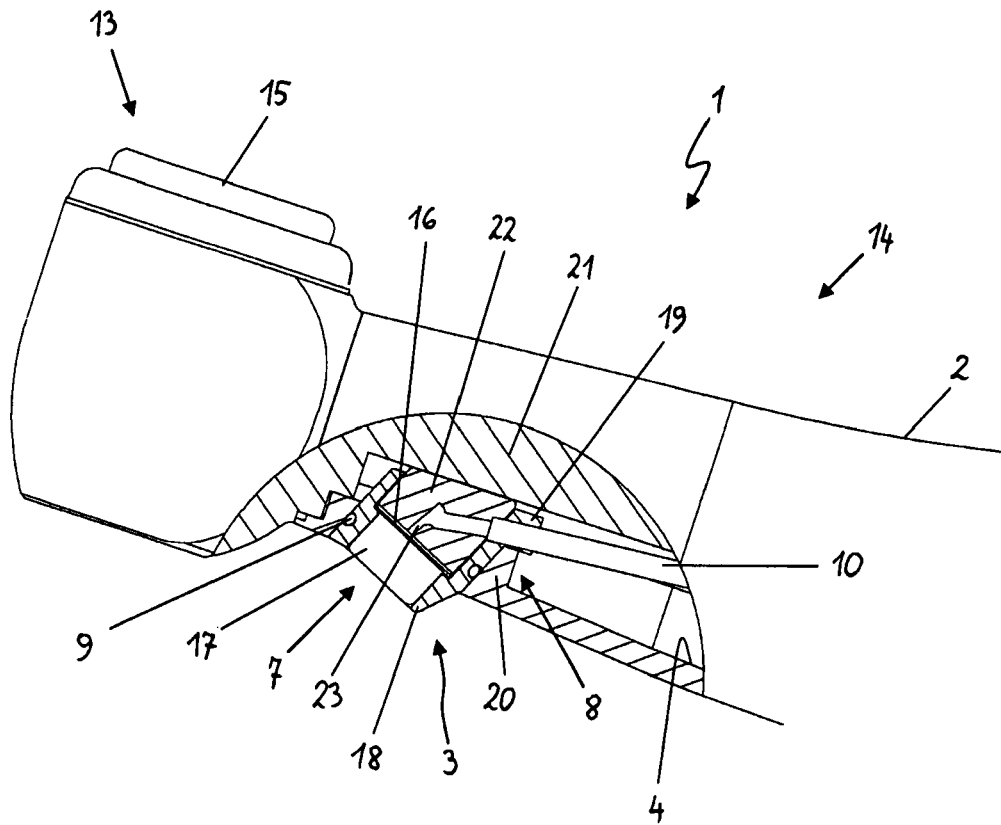
FIG. 2 shows an enlargement of the front section of the handpiece according to FIG. 1.

The medical handpiece 1, in particular the dental handpiece illustrated in FIGS. 1 and 2, comprises a handle part 14 and a head part 13 at an angle to the former. A tool receptacle which can be set in motion, namely rotatably here, is arranged in the head part 13 and can accommodate a tool, e.g., a rotatable drill. The tool is driven by at least one drive element that is connected to the tool, whereby the drive element is preferably designed as a rotating shaft. The drive element may have other components depending on the type of handpiece, e.g., one or more additional rotating or oscillating shafts, one or more gearwheels or gears, a motor, a rotor, a vibration generator, etc.

A pushbutton 15 is provided at one end of the head part 13 for operation of a tool release mechanism, so that a tool which is held or chucked in the tool receptacle can be released from said tool receptacle. A tool opening is provided on the end of the head part 13 opposite the pushbutton 15, so that a tool can be inserted through it into the tool receptacle. The tool thus protrudes out of the head part 13 at an angle to the longitudinal axis of the handle part 14.

A lighting device 3 for emitting radiation onto a preparation site is arranged on the end of the handle part 14 facing the head part 13. The lighting device 3 comprises a lighting module 7 with at least one optical semiconductor element. The lighting module 7 is situated in a light-emitting opening 5 of the outer sleeve 2 of the handpiece 1, whereby most of the lighting module and/or the optical semiconductor element is accommodated in the interior of the handpiece 1. Therefore, the lighting module 7 does not interfere with the handling of the handpiece 1. Due to the arrangement of the lighting module 7 in the immediate vicinity of the head part 13, no waveguide is needed for emitting radiation onto the preparation site.

The at least one optical semiconductor element is accommodated in an interior of the lighting module 7, whereby according to a preferred embodiment, the interior is hermetically sealed with respect to the environment, so that the optical semiconductor element can be subjected to various cleaning and care measures, in particular sterilization, jointly with the handpiece. The hermetically sealed interior is formed by a socket 16 and a cap 17 tightly connected to the former, e.g., by welding. In addition a light-emitting window is provided on the cap 17 through which the radiation generated by the optical semiconductor element can pass. Instead of or connected to the light-emitting window, additional optical elements such as waveguides or lenses may be provided. These optical elements may be designed as part of the lighting module 7 or as separate parts.

The lighting module 7 also comprises a lampholder 18 having a cylindrical, essentially sleeve-shaped form through which a borehole passes. The lampholder 18 is preferably made of a material that does not conduct electricity. The socket 16 and the cap 17 are accommodated in the borehole. In addition, a casting compound body 22, which is made of a synthetic resin, e.g., epoxy resin or silicone resin in particular, is provided in the end of the lampholder 18 facing the interior 4. The casting compound body 22 sheaths the front end of the electric line 10, which is connected to the electric current source, in particular the section of the line 10 that is free of any insulating protective sheath. The casting compound body 22 also surrounds the electric contacts 23 of the optical semiconductor element formed as an LED. The line 10 and the contacts 23 are inseparably joined together by the casting compound body 22. The line 10 and the contacts 23 are preferably additionally soldered, welded or crimped (pinched) together. The casting compound body 22 also seals the lighting module 7 and the contacts 23.

A sealing element 9, e.g., a sealing ring, which is accommodated in a groove on the outer sheath of the lampholder 18, is pinched between the outer sleeve 2 of the handpiece 1 and the outer sheath of the lampholder 18. The sealing element 9 seals the interior 4 of the handpiece 1 and the components contained therein from the environment, preventing the penetration of particles, dirt, treatment media, cleaning agents, etc., into the handpiece 1 or leakage of lubricant out of the interior of the handpiece 1. Alternatively or additionally, such a seal may also be provided on the handpiece 1 itself.

In addition, the fastening device or means 8, which serve to fasten the lighting device 3 to the handpiece 1, are also provided on the lampholder 18. These fastening means may comprise a flange 19, which is arranged on one end of the lampholder 18 and the outer sheath of the lampholder 18. The lighting module 7 is inserted into the light-emitting opening 5, whereby the outer sheath of the lampholder 18 is of such dimensions that it forms a crimped connection to the outer sleeve 2 of the handpiece 1. The outer sleeve 2 has a fastening element 20, e.g., in the form of protrusions, ring shoulders, etc., that extend into the interior 4, to increase the frictional or pinching contact area with the outer sheath of the lampholder 18. If the lampholder 18 is inserted completely into the light-emitting opening 5, then the flange 19 comes in contact with the free end of the fastening element 20, so that on the one hand, additional fixation and, on the other hand, accurate positioning of the lighting module 7 in the light-emitting opening 5 are both achieved.

The fastening of the lighting module 7 in the light-emitting opening 5 is additionally accomplished by the head part 13. The head part 13 has a protrusion 21 on its end facing the handle part 14, said protrusion 21 being insertable into the interior 4 for connecting the head part 13 to the handle part 14.

The protrusion 21 is of such dimensions that, when inserted into the interior 4, it contacts the lighting module 7 and presses in the direction of the light-emitting opening 5, so that the lighting module 7 is fixedly secured in the light-emitting device 5.

The power supply to the at least one optical semiconductor element is provided via the electric pins or contacts 23, the electric line 10 and an electric coupling element 12 which includes additional electric contacts 11. Connection of the handpiece 1 to the power source is accomplished in a known way via a coupling 24, which is preferably designed as a rotary coupling. Other devices such as drive motors, couplings, adaptors, control units, dental units, treatment units, etc., may of course also be provided in a known way between the handpiece 1 and the power source. The electric contacts 11 may be designed differently, depending on the type of coupling 24, e.g., as sliding contacts, spring contacts or pin contacts.

Between the electric coupling element 12 and the contacts 23, other electric or electronic components may be provided in the handpiece 1, in particular a circuit that receives the power supplied by the current source and adapts it to the requirements of the at least one optical semiconductor element. The circuit preferably receives the current of the current source regardless of its polarity and delivers it with a defined polarity to the optical semiconductor element.

The electric coupling element 12, the contacts 11 and optionally also the additional electric or electronic components may likewise be nondetachably connected to the lighting device 3, in particular the lighting module 7, so they can be removed from the handpiece together with the lighting device 3 when the latter is removed. This is an advantage in particular when the additional electric or electronic components perform specific functions, e.g., pulsating delivery of light, which are necessary or appropriate only for certain applications and thus only for certain optical semiconductor elements. Alternatively, the electric coupling element 12, the contacts 11 and optionally also the additional electric or electronic components may also be designed to be detachable from the lighting device 3, so they remain in the handpiece 1 when the lighting device 3 is replaced.

The lighting module 7 is released and replaced via the interior 4 of the handpiece 1 and the coupling opening 6. The light emitting opening 5 which accommodates the lighting module 7 is connected to the coupling opening 6 via the interior 4 of the handpiece 1. To release the lighting module 7, the user must first separate one or more components in the handpiece 1 and/or one or more components of the coupling 24 from the handpiece 1, in particular the coupling pipe 25. In the next step, the user releases the head part 13 of the handpiece 1 from the handle part 14, so that the lighting module 7, which has been forced by the head part 13 into the light-emitting opening 5, can be released from the light-emitting opening 5. The user then exerts pressure on the lighting module 7 from the outside with his finger or an auxiliary tool, so that the lighting module is displaced into the interior 4. Finally, the user removes the lighting module 7 through the coupling opening 6 and preferably also removes the line 10 from the handpiece 1.

The insertion of the lighting module 7 into the handpiece 1 is also accomplished via the interior 4 and the coupling opening 6 in the opposite order from that described for releasing the lighting module 7 from the handpiece 1.

Figure 3:
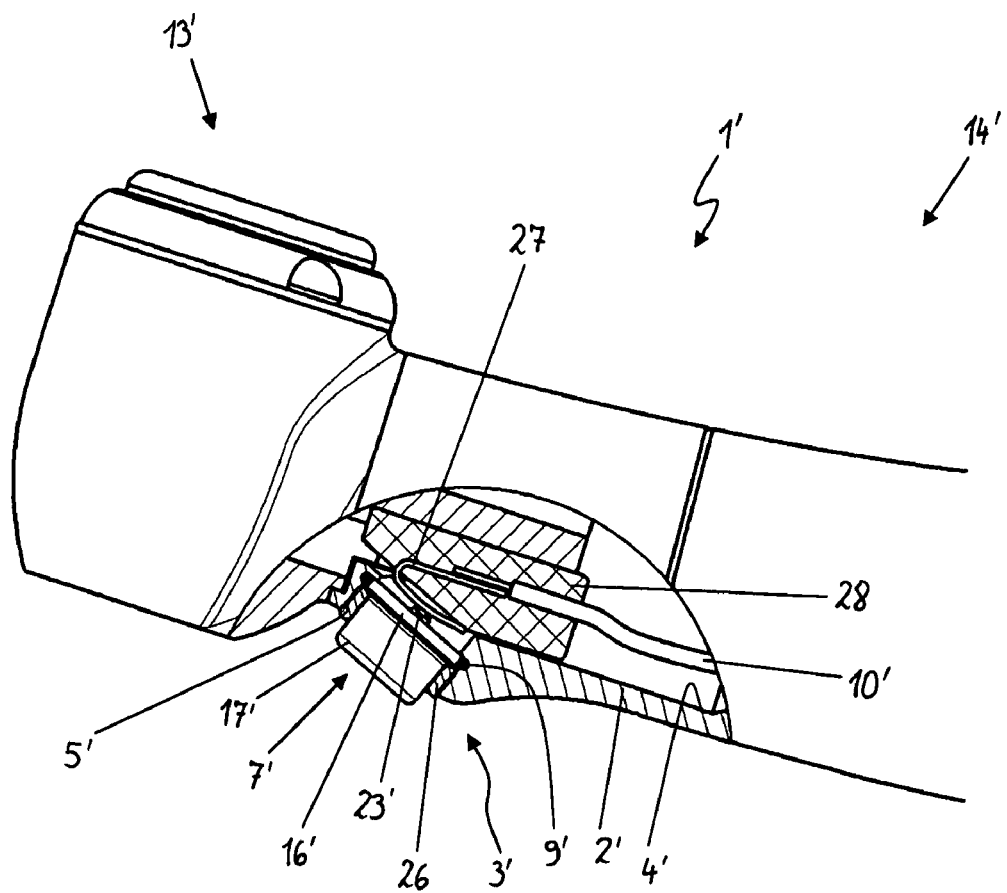
FIG. 3 shows the front section of a second embodiment of a medical handpiece, in particular a dental handpiece with a lighting device that is detachable from the handpiece and comprises at least one optical semiconductor element.

The handpiece 1' depicted in FIG. 3 corresponds in many features to the handpiece 1, so that the differences in particular are described below. Handpiece 1' has a head part 13' and a handle part 14'. Again a light-emitting opening 5' is provided in the outer sleeve 2', with a lighting device 3' and a lighting module 7' having at least one optical semiconductor element accommodated therein being detachably inserted into the light-emitting opening 5'. The lighting module 7' and in particular the at least one optical semiconductor element are arranged essentially in the light-emitting opening 5' of the outer sleeve 2' and thus in the interior of the handpiece 1'.

The power supply of the lighting module 7' is provided via the electric contacts 23' of the LED and an electric line 10' which are connected to one another by a spring-mounted electric contact element 27. The connection between the contacts 23' and the contact element 27 is detachable, so that on removal of the lighting module 7' from the handpiece 1', the line 10' and the contact element 27 remain in the handpiece 1'. An electrically insulating contact holder 28 which is made of a plastic or synthetic resin, for example, surrounds and connects line 10' and contact element 27 and seals the interior 4' of the handpiece 1' from the environment.

In contrast with the handpiece 1 from FIGS. 1 and 2, in the case of the handpiece 1' the lighting module 7' and in particular the at least one optical semiconductor element are replaced through the light-emitting opening 5'. This allows the user an extremely convenient and rapid means of replacing the lighting module 7'.

To replace the lighting module 7', a screw ring 26 is provided having an outside thread on its outside. The outer sleeve 2' is provided with a corresponding inside thread in the area of the light-emitting opening 5', so that the screw ring 26 can be screwed onto the outer sleeve 2'. The lighting module 7' in turn comprises a socket 16' and a cap 17', whereby the socket 16' has a slightly larger diameter than the cap 17'. If the socket 16' and the cap 17' have been joined together, then the outside area of the socket 16' protrudes beyond the cap 17' and forms a ring collar that is secured in the outer sleeve 2' by the screw ring 26 screwed into it. A sealing element 9' is in turn provided in the area of the socket 16', sealing the interior 4' of the handpiece 1' from the environment.

The invention is not limited to the embodiments described here but instead comprises all possible embodiments that do not alter the basic appropriate function principle of the invention. Thus, the shape of the handpiece may differ significantly from the shape shown in FIGS. 1-3; for example, it may be designed to be straight or shaped like a gun. Likewise, the application and functioning of the handpiece may also differ from those in the examples shown here and may pertain to any medical field, in particular dental, surgical or orthopedic field. The type and direction of movement of the tool are also variable and may include, for example, not only rotating tools but also oscillating tools and tools that move back and forth and/or up and down, as well as files, saw blades, chisels, vibrating dental plaque removing tools, rotatable brushes, caps and other prophylactic devices.

There is also the possibility of operating the at least one optical semiconductor element with alternating current above the so-called flicker frequency (corresponding to approximately 25 Hz a.c. voltage), so this gives the human eye the impression of a constant uninterrupted light emission. The a.c. current source may be provided inside the handpiece or outside the handpiece.

What is claimed is:
1. A medical or dental handpiece, comprising:
an outer sleeve;
a tool receptacle for a tool that can be set in motion;
at least one drive element to set the tool in motion; and
a lighting device for emitting radiation onto a preparation site, wherein the lighting device comprises at least one optical semiconductor element which is arranged at least partially in the interior of the handpiece in a light emitting position in which the at least one optical semiconductor element is disposed such that it can be supplied with electric energy and can emit radiation such that the radiation can be directed toward a treatment area and which is detachably connected to the handpiece, wherein an opening is provided in the outer sleeve of the handpiece and is configured so that the at least one optical semiconductor element can be passed through this opening, wherein the opening for passing through the at least one optical semiconductor element is configured as a coupling opening of a rotary coupling, said rotary coupling being arranged at an end of the handpiece opposite to a head part of the handpiece, so that the at least one optical semiconductor element can be moved from said light emitting position through the interior of the handpiece towards said opening and through said opening to remove the at least one optical semiconductor element through said opening.

2. The handpiece according to claim 1, wherein the handpiece comprises at least one component which blocks the interior space through which the at least one optical semiconductor element is movable toward the opening and wherein said at least one component is arranged detachably and/or movably in the handpiece, so that the optical semiconductor element can be moved through the interior space of the handpiece while or after the at least one component is/was moved or removed.

3. The handpiece according to claim 2, wherein the head part or at least one component of a coupling are detachably or movably arranged in the handpiece.

4. The handpiece according to claim 1, wherein the at least one optical semiconductor element is configured as part of a lighting module, wherein the at least one optical semiconductor element is releasable from the handpiece together with the lighting module.

5. The handpiece according to claim 4, wherein the lighting module comprises an interior that is hermetically sealed toward the outside to receive the at least one optical semiconductor element.

6. The handpiece according to claim 4, wherein the lighting module comprises fastening means for detachably connecting the lighting module to the handpiece.

7. The handpiece according to claim 4, wherein the lighting module comprises at least one sealing element for sealing an interior of the handpiece with respect to the environment.

8. The handpiece according to claim 7, wherein the at least one sealing element comprises a casting compound body, which covers electric contacts of the lighting module, and an electric line, which connects the lighting module to an electric current source.

9. The handpiece according to claim 1, wherein the handpiece comprises a light emitting opening which accommodates the lighting device and wherein the interior of the handpiece connects the light emitting opening to the opening for passing through the at least one optical semiconductor element.

10. The handpiece according to claim 1, wherein the at least one optical semiconductor element or a lighting module comprising the at least one optical semiconductor element is connected to other components, wherein at least one of these components can be released from the handpiece together with the at least one optical semiconductor element or the lighting module and wherein the other components comprise at least one of a waveguide, an optical element, a lens, an electric or electronic component, an electric line, electric contacts, a carrier device, a circuit board, and electric coupling elements.

11. The handpiece according to claim 1, wherein the lighting device is arranged adjacent the head part of the handpiece.

12. A medical or dental handpiece, comprising:
an outer sleeve;
a tool receptacle for a tool that can be set in motion;
at least one drive element to set the tool in motion; and
a lighting device for emitting radiation onto a preparation site, wherein the lighting device comprises at least one optical semiconductor element which is arranged at least partially in the interior of the handpiece and which is detachably connected to the handpiece, the handpiece further comprising an electric line for supplying electric power to electric contacts of the at least one optical semiconductor element, wherein the electric contacts and the electric line are encased by a single, integral body of encasing material such that the encasing material connects the electric contacts undetachably to the electric line and seals an interface between the electric contacts and the electric line without providing an access to said interface.

13. The handpiece according to claim 12, wherein the electric contacts or electric pins and the electric line are soldered, welded or crimped together.

14. The handpiece according to claim 12, wherein the encasing material comprises a casting compound body.

15. The handpiece according to claim 14, wherein the electric line comprises a section with an insulating protective sheath and a section which is free of an insulating protective sheath, wherein the section which is free of an insulating protective sheath comprises a contact segment which contacts the electric contacts pins of the at least one optical semiconductor element and a connecting segment which connects to the section with an insulating protective sheath and wherein the casting compound body encases the section of the electric line, which is free of an insulating protective sheath including the contact segment and the connecting segment.

16. The handpiece according to claim 14, wherein the at least one optical semiconductor element is designed as part of a lighting module and wherein the casting compound body is disposed adjacent the lighting module.

17. The handpiece according to claim 16, wherein the lighting module comprises an interior that is hermetically sealed toward the outside to receive the at least one optical semiconductor element.

18. The handpiece according to claim 16, wherein the lighting module comprises an electrically insulating lampholder.

19. The handpiece according to claim 14, wherein the handpiece comprises a head part and a handle part, the head part comprising a protrusion for connecting the head part to the handle part, and wherein the protrusion contacts the casting compound body in order to push the casting compound body towards a light-emitting opening in the outer sleeve of the handpiece.

20. The handpiece according to claim 14, further comprising a lamp holder which surrounds at least partially the at least one optical semiconductor element, the casting compound body, the electric contacts and the electric line.

21. The handpiece according to claim 20, wherein the casting compound body is cast into the lamp holder in order achieve a substantially fluid and vapour tight seal.

22. The handpiece according to claim 12, wherein the handpiece is designed so that the at least one optical semiconductor element is movable through an interior space of the handpiece.

23. A medical or dental handpiece, comprising:
a head part and a handle part;

an outer sleeve;
a tool receptacle for a tool that can be set in motion;
at least one drive element to set the tool in motion; and
a lighting device for emitting radiation onto a preparation site, wherein the lighting device comprises at least one optical semiconductor element which is arranged at least partially in the interior of the handpiece and which is detachably connected to the handpiece, wherein the handle part comprises a first section adjacent the head part and a second section adjacent the first section, wherein the first section and the second section are arranged at an angle relative to each other and wherein the handpiece is designed so that the at least one optical semiconductor element is movable through an interior space of the handpiece thereby passing through the angle between the first section and the second section and through the second section, so that the at least one optical semiconductor element can be removed from the handpiece by moving it through the angle first and then through the second section.

24. The handpiece according to claim 23, wherein the second section comprises an opening which is configured so that the at least one optical semiconductor element can be passed through this opening, wherein the opening for passing through the at least one optical semiconductor element is configured as a coupling opening.

25. The handpiece according to claim 23, wherein the at least one optical semiconductor element is configured as part of a lighting module, wherein the at least one optical semiconductor element is releasable from the handpiece together with the lighting module and wherein the lighting module comprises an interior that is hermetically sealed toward the outside to receive the at least one optical semiconductor element.

26. The handpiece according to claim 25, wherein the lighting module comprises at least one sealing element for sealing an interior of the handpiece with respect to the environment, said sealing element comprising a casting compound body.

27. The handpiece according to claim 23, wherein the handpiece comprises a light emitting opening which accommodates the lighting device and wherein the interior space of the handpiece connects the light emitting opening to a coupling opening for passing through the at least one optical semiconductor element.

28. The handpiece according to claim 23, wherein the handpiece comprises at least one component which blocks the interior space through which the at least one optical semiconductor element is movable toward an opening in the outer sleeve of the handpiece and wherein said at least one component is arranged detachably and/or movably in the handpiece, so that the optical semiconductor element can be moved through the interior space of the handpiece while or after the at least one component is / was moved or removed.

29. The handpiece according to claim 28, wherein the head part or at least one component of a coupling are detachably or movably arranged in the handpiece.

30. A medical or dental handpiece, comprising:
an outer sleeve;
a tool receptacle for a tool that can be set in motion;
at least one drive element to set the tool in motion; and
a lighting device for emitting radiation onto a preparation site, wherein the lighting device comprises at least one optical semiconductor element which is arranged at least partially in the interior of the handpiece and which is detachably connected to the handpiece, wherein an opening is provided in the outer sleeve of the handpiece and is configured so that the at least one optical semiconductor element can be passed through this opening, wherein the handpiece comprises a light emitting opening which accommodates the lighting device and wherein the interior of the handpiece connects the light emitting opening to the opening for passing through the at least one optical semiconductor element, so that the at least one optical semiconductor element can be moved from the light emitting opening through the interior of the handpiece towards and through said opening for passing through the at least one optical semiconductor element to remove the at least one optical semiconductor element through said opening from the handpiece.

31. The handpiece according to claim 30, wherein the handpiece comprises at least one component which blocks the interior space through which the at least one optical semiconductor element is movable toward the opening for passing through the at least one optical semiconductor element and wherein said at least one component is arranged detachably and/or movably in the handpiece, so that the optical semiconductor element can be moved through the interior space of the handpiece while or after the at least one component is/was moved or removed.

32. A medical or dental handpiece, comprising:
a first end comprising a head part;
a second end, a body extending between the first end and the second end;
an outer sleeve, a tool receptacle for a tool that can be set in motion;
at least one drive element to set the tool in motion; and
a lighting device for emitting radiation onto a preparation site, wherein the lighting device comprises at least one optical semiconductor element which is arranged at least partially in the interior of the handpiece and which is detachably connected to the handpiece, wherein the handpiece is designed so that the at least one optical semiconductor element is movable through an interior space of the handpiece, wherein the handpiece comprises at least one component which is connected or coupled detachably to the handpiece or arranged movably in the handpiece, wherein said at least one component is disposed such that it prevents the at least one optical semiconductor element to be detached from the handpiece when the at least one component takes its position at the handpiece, and wherein while or after moving or removing the at least one component the at least one optical semiconductor element can be moved through the interior of the handpiece, wherein the at least one component comprises a component of a coupling which is arranged at the second end of the handpiece and wherein the coupling comprises an opening which is configured so that the at least one optical semiconductor element can be passed through this opening.

33. The handpiece according to claim 32, wherein the coupling comprises a rotary coupling.

34. The handpiece according to claim 32, wherein the at least one optical semiconductor element is configured as part of a lighting module, wherein the at least one optical semiconductor element is releasable from the handpiece together with the lighting module and wherein the lighting module comprises an interior that is hermetically sealed toward the outside to receive the at least one optical semiconductor element.

35. The handpiece according to claim 32, wherein the at least one optical semiconductor element is configured as part of a lighting module, wherein the at least one optical semiconductor element is releasable from the handpiece together with the lighting module and wherein the lighting module comprises at least one sealing element for sealing an interior of the handpiece with respect to the environment.

36. The handpiece according to claim 35, wherein the at least one sealing element comprises a casting compound body, which covers electric contacts of the lighting module, and an electric line, which connects the lighting module to an electric current source.

* * * * *

UNITED STATES PATENT AND TRADEMARK OFFICE
CERTIFICATE OF CORRECTION

PATENT NO. : 8,038,439 B2
APPLICATION NO. : 11/998134
DATED : October 18, 2011
INVENTOR(S) : Norbert Schatz and Karl Schmiedlechner Page 1 of 1

It is certified that error appears in the above-identified patent and that said Letters Patent is hereby corrected as shown below:

In the Specification:

Column 6, line 45, "serve" should read --serves--.

Column 6, line 46, "are" should read --is--.

Column 7, line 5, "device" should read --opening--.

In the Claims:

Claim 13, column 10, line 22, "contacts or electric pins and" should read --contacts and--.

Claim 15, column 10, line 31, "contacts pins of" should read --contacts of--.

Claim 21, column 10, lines 60-61, "in order achieve" should read --in order to achieve--.

Signed and Sealed this
Tenth Day of April, 2012

David J. Kappos
*Director of the United States Patent and Trademark Office*